United States Patent [19]

Grossmann et al.

[11] Patent Number: 5,171,352
[45] Date of Patent: Dec. 15, 1992

[54] AGENTS FOR DEFOLIATING COTTON

[76] Inventors: Klaus Grossmann, 5 Wilhelm-Busch-Strasse; Wilhelm Rademacher, 1 Austrasse, both of 6703 Limburgerhof; Gerhard Hamprecht, 28 Rote-Turm-Strasse, 6940 Weinheim; Karl-Otto Westphalen, 58 Mausbergweg, 6720 Speyer; Bruno Wuerzer, 13 Ruedigerstrasse, 6701 Otterstadt, all of Fed. Rep. of Germany

[21] Appl. No.: 561,611

[22] Filed: Aug. 2, 1990

[30] Foreign Application Priority Data

Aug. 7, 1989 [DE] Fed. Rep. of Germany ....... 3926058

[51] Int. Cl.⁵ .................... A01N 31/08; A01N 43/54; A01N 43/64
[52] U.S. Cl. ......................................... 71/72; 71/74; 71/92
[58] Field of Search ............................... 71/74, 92, 72

[56] References Cited

U.S. PATENT DOCUMENTS 4,127,405 11/1978 Levitt ........................... 71/93
4,659,366 4/1987 Stetter et al. .................. 71/92

FOREIGN PATENT DOCUMENTS 0007687 2/1980 European Pat. Off.
0136061 1/1988 European Pat. Off.
0291851 11/1988 European Pat. Off.
0318620 6/1989 European Pat. Off.
3413565 10/1985 Fed. Rep. of Germany.
3413490 10/1986 Fed. Rep. of Germany.
3905916 8/1990 Fed. Rep. of Germany.

OTHER PUBLICATIONS

Proc. Br, Crop Protection Conference—Weeds, (1980) vol. 1 pp. 7–14.

Primary Examiner—Richard L. Raymond
Assistant Examiner—S. Mark Clardy

[57] ABSTRACT

Cotton plants are defoliated by the action of an amount, having a defoliant effect, of a phenylsulfonylurea Ia or Ib

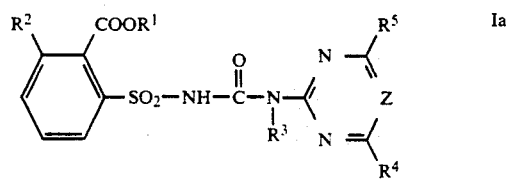

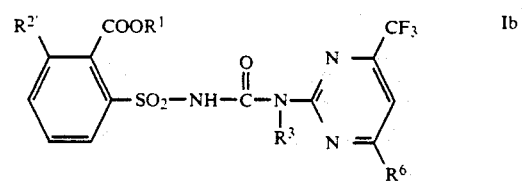

where $R^1$ is $C_1$–$C_4$-alkyl or $C_3$–$C_5$-alkoxyalkyl, and these radicals may each carry from 1 to 3 halogen atoms, or $C_3$- or $C_4$-alkenyl or $C_3$- or $C_4$-alkynyl, $R^2$ is F, Cl or Br, $R^{2'}$ is H, F, Cl or Br, $R^3$ is H, $CH_3$ or $C_2H_5$, $R^4$ is halogen, $CH_3$ or $OCH_3$, $R^5$ is $CH_3$ or $OCH_3$, $R^6$ is halogen, $C_1$- or $C_2$-alkyl, $C_1$- or $C_2$-alkoxy, $C_1$- or $C_2$-alkylthio or $C_1$- or $C_2$-alkylamino and Z is CH or N, or of an alkali metal or alkaline earth metal salt of a compound Ia or Ib.

5 Claims, No Drawings

AGENTS FOR DEFOLIATING COTTON

The present invention relates to a method for defoliating cotton plants, wherein an amount, having a defoliant effect, of a phenylsulfonylurea of the general formula Ia or Ib

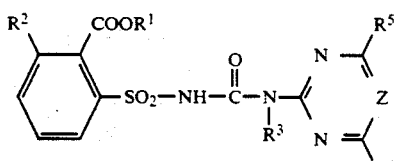

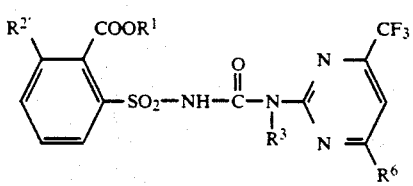

where $R^1$ is $C_1$–$C_4$-alkyl or $C_3$–$C_5$-alkoxyalkyl, and these radicals may each carry up to 3 halogen atoms, or $C_3$- or $C_4$-alkenyl or $C_3$- or $C_4$-alkynyl, $R^2$ is fluorine, chlorine or bromine, $R^{2'}$ is hydrogen, fluorine, chlorine or bromine, $R^3$ is hydrogen, methyl or ethyl, $R^4$ is halogen, methyl or methoxy, $R^5$ is methyl or methoxy, $R^6$ is halogen, $C_1$- or $C_2$-alkyl, $C_1$- or $C_2$-alkoxy, $C_1$- or $C_2$-alkylthio or $C_1$- or $C_2$-alkylamino and Z is CH or N, or an alkali metal or alkaline earth metal salt of a compound Ia or Ib is allowed to act on cotton plants.

The present invention furthermore relates to an agent for defoliating cotton plants, containing, in addition to conventional additives, a phenylsulfonylurea Ia or Ib or an alkali metal or alkaline earth metal salt thereof and, as a synergistic agent, a compound from the series consisting of the N-phenyl-3,4,5,6-tetrahydrophthalimides (II).

DE-A 3 413 565 discloses the defoliant effect of phenylsulfonylureas which carry in the ortho-position to the sulfonyl group, inter alia, alkoxy or alkenyloxy radicals having terminal heterocyclic subtituents. However, example C reveals that the falling of the leaves is accompanied by simultaneous drying out of the leaves.

U.S. Pat. No. 4,127,405 describes the herbicidal action of phenylsulfonylureas whose phenyl ring is unsubstituted or substituted by fluorine atoms in the ortho-position to the sulfonyl group on bush beans, a defoliant effect being described as an accompanying symptom of the action. However, the defoliant effect on cotton plants is poor.

Furthermore, EP-A 0 291 851 and EP-A 136 061 describe phenylsulfonylureas having an alkoxycarbonyl group in the ortho-position to the sulfonyl group. However, only their herbicidal and growth-regulating action is described there.

EP-A 0 318 620 discloses phenylsulfonylureas having an alkoxycarbonyl group in the ortho-position to the sulfonyl group and possessing a heteroaliphatic radical in the meta-position. However, only herbicidal and growth-regulating properties are described for these substances, a growth-inhibiting action being stated in the case of cotton.

Phenylsulfonylureas having, in the ortho-position to the sulfonyl group, an alkoxycarbonyl group whose alkoxy radical carries an oxime radical are disclosed in DE-A 34 13 490. Although the possible use of these compounds as defoliants is pointed out, their good tolerance by crops is specially mentioned, cotton being singled out.

EP-A 7687 discloses the defoliant effect on bush beans of phenylsulfonylureas which carry an alkoxycarbonyl radical in the ortho-position to the sulfonyl group. For cotton plants, no defoliant effect but merely a herbicidal action is mentioned.

It is also known that, in general, the biological action of sulfonylureas is very slow to begin. For example, Proc. Br. Crop. Prot. Conf. Weeds 1980, I 7–14 states that, in the case of treatment with the sulfonylurea 2-chloro-N-[[(4-methoxy-6-methyl-1,3,5-triazin-2-yl)-amino]-carbonyl]-benzenesulfonamide, the herbicidal effect or the dying of sensitive plants takes place slowly and is accompanied by chloroses, necroses, the dying of shoots and decoloration of the leaf nerves.

N-Phenyl-3,4,5,6-tetrahydrophthalimides for the desiccation and abscission of plant organs are described in German Patent Application DE-A 39 05 916.

There is considerable commercial interest in both abscission agents and desicants for facilitating harvesting. Particularly in intensive cotton cultivation, the use of defoliants is necessary for effective use of plucking machines for harvesting the bolls. For reasons relating to harvesting, defoliation in the form of green leaf parts is preferred to pure desiccation and withering of the remaining plant, since otherwise the fiber quality is very adversely affected by soiling due to withered leaf residues. Furthermore, the defoliants used to date do not satisfactorily prevent resprouting of the leaves.

It is an object of the present invention to provide a novel and better method for defoliating cotton plants and novel and better defoliants, especially for cotton.

We have found that this object is achieved by the method, defined at the outset, for defoliating cotton plants. We have also found agents for defoliating cotton which do not have the abovementioned disadvantages.

Preferred compounds Ia or Ib are those in which the substituents have the following meanings:

$R^1$ is $C_1$–$C_4$-alkyl, such as methyl, ethyl, n-propyl, isopropyl, n-butyl, isobutyl, sec-butyl or tert-butyl, $C_3$-or $C_4$-alkenyl, in particular 2-propenyl, $C_3$- or $C_4$-alkynyl, in particular 2-propynyl, $C_1$–$C_4$-haloalkyl, in particular 2-chloroethyl, $C_3$–$C_5$-alkoxyalkyl, in particular 2-methoxyethyl, or $C_4$- or $C_5$-haloalkoxyalkyl, in particular 2-(2-chloroethoxy)-ethyl;

$R^2$ is fluorine, chlorine or bromine;

$R^{2'}$ is hydrogen, fluorine, chlorine or bromine;

$R^3$ is hydrogen, methyl or ethyl;

$R^4$ is halogen, in particular chlorine, methyl or methoxy;

$R^5$ is methyl or methoxy and $R^6$ is halogen, in particular chlorine, methyl, ethyl, methoxy, ethoxy, methylthio, ethylthio, methylamino or ethylamino.

Compounds Ia and Ib which are suitable as defoliants for cotton are shown in Tables 1 and 2. Tables 3 and 4 list the particularly preferred compounds of this class.

TABLE 1

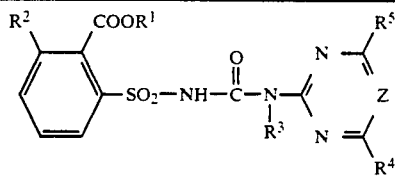

| Compound No. | $R^1$ | $R^2$ | $R^3$ | $R^4$ | $R^5$ | Z | mp. [°C.] |
|---|---|---|---|---|---|---|---|
| 1.1 | $CH_3$ | Cl | H | $CH_3$ | $CH_3$ | CH | 215–217 |
| 1.2 | $C_2H_5$ | Cl | H | $CH_3$ | $CH_3$ | CH | 198–200 |
| 1.3 | $n-C_3H_7$ | Cl | H | $CH_3$ | $CH_3$ | CH | |
| 1.4 | $i-C_3H_7$ | Cl | H | $CH_3$ | $CH_3$ | CH | 200–202 |
| 1.5 | $n-C_4H_9$ | Cl | H | $CH_3$ | $CH_3$ | CH | |
| 1.6 | $i-C_4H_9$ | Cl | H | $CH_3$ | $CH_3$ | CH | |
| 1.7 | $sec.-C_4H_9$ | Cl | H | $CH_3$ | $CH_3$ | CH | |
| 1.8 | $CH_2-CH=CH_2$ | Cl | H | $CH_3$ | $CH_3$ | CH | |
| 1.9 | $CH_2-C\equiv CH$ | Cl | H | $CH_3$ | $CH_3$ | CH | |
| 1.10 | $CH_2-CH_2-Cl$ | Cl | H | $CH_3$ | $CH_3$ | CH | |
| 1.11 | $CH_2-CH_2-O-CH_3$ | Cl | H | $CH_3$ | $CH_3$ | CH | |
| 1.12 | $CH_2-CH_2-O-CH_2-CH_2Cl$ | Cl | H | $CH_3$ | $CH_3$ | CH | |
| 1.13 | $CH_3$ | F | H | $CH_3$ | $CH_3$ | CH | 212–214 |
| 1.14 | $C_2H_5$ | F | H | $CH_3$ | $CH_3$ | CH | |
| 1.15 | $i-C_3H_7$ | F | H | $CH_3$ | $CH_3$ | CH | |
| 1.16 | $n-C_4H_9$ | F | H | $CH_3$ | $CH_3$ | CH | |
| 1.17 | $i-C_4H_9$ | F | H | $CH_3$ | $CH_3$ | CH | |
| 1.18 | $sec.-C_4H_9$ | F | H | $CH_3$ | $CH_3$ | CH | |
| 1.19 | $CH_2-CH=CH_2$ | F | H | $CH_3$ | $CH_3$ | CH | |
| 1.20 | $CH_2-C\equiv CH$ | F | H | $CH_3$ | $CH_3$ | CH | |
| 1.21 | $CH_2-CH_2-Cl$ | F | H | $CH_3$ | $CH_3$ | CH | |
| 1.22 | $CH_2-CH_2-O-CH_3$ | F | H | $CH_3$ | $CH_3$ | CH | 158–160 |
| 1.23 | $CH_2-CH_2-O-CH_2-CH_2Cl$ | F | H | $CH_3$ | $CH_3$ | CH | |
| 1.24 | $CH_3$ | Cl | H | Cl | $OCH_3$ | CH | 213 (decomp.) |
| 1.25 | $C_2H_5$ | Cl | H | Cl | $OCH_3$ | CH | 179–182 |
| 1.26 | $n-C_3H_7$ | Cl | H | Cl | $OCH_3$ | CH | 181–184 |
| 1.27 | $i-C_3H_7$ | Cl | H | Cl | $OCH_3$ | CH | 210–212 |
| 1.28 | $n-C_4H_9$ | Cl | H | Cl | $OCH_3$ | CH | |
| 1.29 | $i-C_4H_9$ | Cl | H | Cl | $OCH_3$ | CH | |
| 1.30 | $sec.-C_4H_9$ | Cl | H | Cl | $OCH_3$ | CH | |
| 1.31 | $CH_2-CH=CH_2$ | Cl | H | Cl | $OCH_3$ | CH | |
| 1.32 | $CH_2-C\equiv CH$ | Cl | H | Cl | $OCH_3$ | CH | |
| 1.33 | $CH_2-CH_2Cl$ | Cl | H | Cl | $OCH_3$ | CH | 169–171 |
| 1.34 | $CH_2-CH_2-O-CH_3$ | Cl | H | Cl | $OCH_3$ | CH | 168–170 |
| 1.35 | $CH_2-CH_2-O-CH_2-CH_2Cl$ | Cl | H | Cl | $OCH_3$ | CH | 161–164 |
| 1.36 | $CH_3$ | F | H | Cl | $OCH_3$ | CH | 215–217 |
| 1.37 | $C_2H_5$ | F | H | Cl | $OCH_3$ | CH | 210–213 |
| 1.38 | $n-C_3H_7$ | F | H | Cl | $OCH_3$ | CH | 195–196 |
| 1.39 | $i-C_3H_7$ | F | H | Cl | $OCH_3$ | CH | |
| 1.40 | $n-C_4H_9$ | F | H | Cl | $OCH_3$ | CH | |
| 1.41 | $i-C_4H_9$ | F | H | Cl | $OCH_3$ | CH | |
| 1.42 | $sec.-C_4H_9$ | F | H | Cl | $OCH_3$ | CH | |
| 1.43 | $CH_2-CH=CH_2$ | F | H | Cl | $OCH_3$ | CH | |
| 1.44 | $CH_2-C\equiv CH$ | F | H | Cl | $OCH_3$ | CH | |
| 1.45 | $CH_2-CH_2Cl$ | F | H | Cl | $OCH_3$ | CH | |
| 1.46 | $CH_2-CH_2-O-CH_3$ | F | H | Cl | $OCH_3$ | CH | 175–177 |
| 1.47 | $CH_2-CH_2-O-CH_2-CH_2Cl$ | F | H | Cl | $OCH_3$ | CH | |
| 1.48 | $CH_3$ | Cl | H | $OCH_3$ | $OCH_3$ | CH | 227–230 |
| 1.49 | $C_2H_5$ | Cl | H | $OCH_3$ | $OCH_3$ | CH | 210–212 |
| 1.50 | $n-C_3H_7$ | Cl | H | $OCH_3$ | $OCH_3$ | CH | 217–219 |
| 1.51 | $i-C_3H_7$ | Cl | H | $OCH_3$ | $OCH_3$ | CH | 202–205 |
| 1.52 | $n-C_4H_9$ | Cl | H | $OCH_3$ | $OCH_3$ | CH | |
| 1.53 | $i-C_4H_9$ | Cl | H | $OCH_3$ | $OCH_3$ | CH | |
| 1.54 | $sec.-C_4H_9$ | Cl | H | $OCH_3$ | $OCH_3$ | CH | |
| 1.55 | $CH_2-CH=CH_2$ | Cl | H | $OCH_3$ | $OCH_3$ | CH | 197 (decomp.) |
| 1.56 | $CH_2-C\equiv CH$ | Cl | H | $OCH_3$ | $OCH_3$ | CH | |
| 1.57 | $CH_2-CH_2Cl$ | Cl | H | $OCH_3$ | $OCH_3$ | CH | |
| 1.58 | $CH_2-CH_2-O-CH_3$ | Cl | H | $OCH_3$ | $OCH_3$ | CH | 173–175 |
| 1.59 | $CH_2-CH_2-O-CH_2-CH_2Cl$ | Cl | H | $OCH_3$ | $OCH_3$ | CH | |
| 1.60 | $CH_3$ | F | H | $OCH_3$ | $OCH_3$ | CH | 204–206 |
| 1.61 | $C_2H_5$ | F | H | $OCH_3$ | $OCH_3$ | CH | |
| 1.62 | $n-C_3H_7$ | F | H | $OCH_3$ | $OCH_3$ | CH | |
| 1.63 | $i-C_3H_7$ | F | H | $OCH_3$ | $OCH_3$ | CH | |
| 1.64 | $n-C_4H_9$ | F | H | $OCH_3$ | $OCH_3$ | CH | |
| 1.65 | $i-C_4H_9$ | F | H | $OCH_3$ | $OCH_3$ | CH | |
| 1.66 | $sec.-C_4H_9$ | F | H | $OCH_3$ | $OCH_3$ | CH | |
| 1.67 | $CH_2-CH=CH_2$ | F | H | $OCH_3$ | $OCH_3$ | CH | |
| 1.68 | $CH_2-C\equiv CH$ | F | H | $OCH_3$ | $OCH_3$ | CH | |
| 1.69 | $CH_2-CH_2Cl$ | F | H | $OCH_3$ | $OCH_3$ | CH | |
| 1.70 | $CH_2-CH_2-O-CH_3$ | F | H | $OCH_3$ | $OCH_3$ | CH | |
| 1.71 | $CH_2-CH_2-O-CH_2-CH_2Cl$ | F | H | $OCH_3$ | $OCH_3$ | CH | |

TABLE 1-continued

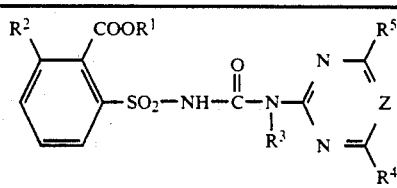

| Compound No. | R$^1$ | R$^2$ | R$^3$ | R$^4$ | R$^5$ | Z | mp. [°C.] |
|---|---|---|---|---|---|---|---|
| 1.72 | CH$_3$ | Cl | H | CH$_3$ | OCH$_3$ | CH | 210–214 |
| 1.73 | C$_2$H$_5$ | Cl | H | CH$_3$ | OCH$_3$ | CH | 193–195 |
| 1.74 | n-C$_3$H$_7$ | Cl | H | CH$_3$ | OCH$_3$ | CH | 178–180 |
| 1.75 | i-C$_3$H$_7$ | Cl | H | CH$_3$ | OCH$_3$ | CH | 205–207 |
| 1.76 | n-C$_4$H$_9$ | Cl | H | CH$_3$ | OCH$_3$ | CH | |
| 1.77 | i-C$_4$H$_9$ | Cl | H | CH$_3$ | OCH$_3$ | CH | |
| 1.78 | sec.-C$_4$H$_9$ | Cl | H | CH$_3$ | OCH$_3$ | CH | |
| 1.79 | CH$_2$—CH=CH$_2$ | Cl | H | CH$_3$ | OCH$_3$ | CH | |
| 1.80 | CH$_2$—C≡CH | Cl | H | CH$_3$ | OCH$_3$ | CH | |
| 1.81 | CH$_2$—CH$_2$Cl | Cl | H | CH$_3$ | OCH$_3$ | CH | 153 (decomp.) |
| 1.82 | CH$_2$—CH$_2$—O—CH$_3$ | Cl | H | CH$_3$ | OCH$_3$ | CH | 154–156 |
| 1.83 | CH$_2$—CH$_2$—O—CH$_2$—CH$_2$Cl | Cl | H | CH$_3$ | OCH$_3$ | CH | 149–151 |
| 1.84 | CH$_3$ | F | H | CH$_3$ | OCH$_3$ | CH | 190–192 |
| 1.85 | C$_2$H$_5$ | F | H | CH$_3$ | OCH$_3$ | CH | |
| 1.86 | n-C$_3$H$_7$ | F | H | CH$_3$ | OCH$_3$ | CH | |
| 1.87 | i-C$_3$H$_7$ | F | H | CH$_3$ | OCH$_3$ | CH | |
| 1.88 | n-C$_4$H$_9$ | F | H | CH$_3$ | OCH$_3$ | CH | |
| 1.89 | i-C$_4$H$_9$ | F | H | CH$_3$ | OCH$_3$ | CH | |
| 1.90 | sec.-C$_4$H$_9$ | F | H | CH$_3$ | OCH$_3$ | CH | |
| 1.91 | CH$_2$—CH=CH$_2$ | F | H | CH$_3$ | OCH$_3$ | CH | |
| 1.92 | CH$_2$—C≡CH | F | H | CH$_3$ | OCH$_3$ | CH | |
| 1.93 | CH$_2$—CH$_2$Cl | F | H | CH$_3$ | OCH$_3$ | CH | 170–171 |
| 1.94 | CH$_2$—CH$_2$—O—CH$_3$ | F | H | CH$_3$ | OCH$_3$ | CH | 160–162 |
| 1.95 | CH$_2$—CH$_2$—O—CH$_2$—CH$_2$Cl | F | H | CH$_3$ | OCH$_3$ | CH | |
| 1.96 | CH$_3$ | Cl | H | CH$_3$ | OCH$_3$ | N | |
| 1.97 | C$_2$H$_5$ | Cl | H | CH$_3$ | OCH$_3$ | N | 192–194 |
| 1.98 | n-C$_3$H$_7$ | Cl | H | CH$_3$ | OCH$_3$ | N | 179–181 |
| 1.99 | i-C$_3$H$_7$ | Cl | H | CH$_3$ | OCH$_3$ | N | 197–198 |
| 1.100 | n-C$_4$H$_9$ | Cl | H | CH$_3$ | OCH$_3$ | N | |
| 1.101 | i-C$_4$H$_9$ | Cl | H | CH$_3$ | OCH$_3$ | N | |
| 1.102 | sec.-C$_4$H$_9$ | Cl | H | CH$_3$ | OCH$_3$ | N | |
| 1.103 | CH$_2$—CH=CH$_2$ | Cl | H | CH$_3$ | OCH$_3$ | N | |
| 1.104 | CH$_2$—C≡CH | Cl | H | CH$_3$ | OCH$_3$ | N | |
| 1.105 | CH$_2$—CH$_2$Cl | Cl | H | CH$_3$ | OCH$_3$ | N | |
| 1.106 | CH$_2$—CH$_2$—O—CH$_3$ | Cl | H | CH$_3$ | OCH$_3$ | N | |
| 1.107 | CH$_2$—CH$_2$—O—CH$_2$—CH$_2$Cl | Cl | H | CH$_3$ | OCH$_3$ | N | |
| 1.108 | CH$_3$ | F | H | CH$_3$ | OCH$_3$ | N | 212–213 |
| 1.109 | C$_2$H$_5$ | F | H | CH$_3$ | OCH$_3$ | N | 196 (decomp.) |
| 1.110 | n-C$_3$H$_7$ | F | H | CH$_3$ | OCH$_3$ | N | 196–199 |
| 1.111 | i-C$_3$H$_7$ | F | H | CH$_3$ | OCH$_3$ | N | 199–201 |
| 1.112 | n-C$_4$H$_9$ | F | H | CH$_3$ | OCH$_3$ | N | |
| 1.113 | i-C$_4$H$_9$ | F | H | CH$_3$ | OCH$_3$ | N | |
| 1.114 | sec.-C$_4$H$_9$ | F | H | CH$_3$ | OCH$_3$ | N | |
| 1.115 | CH$_2$—CH=CH$_2$ | F | H | CH$_3$ | OCH$_3$ | N | |
| 1.116 | CH$_2$—C≡CH | F | H | CH$_3$ | OCH$_3$ | N | |
| 1.117 | CH$_2$—CH$_2$Cl | F | H | CH$_3$ | OCH$_3$ | N | |
| 1.118 | CH$_2$—CH$_2$—O—CH$_3$ | F | H | CH$_3$ | OCH$_3$ | N | 153–156 |
| 1.119 | CH$_2$—CH$_2$—O—CH$_2$—CH$_2$Cl | F | H | CH$_3$ | OCH$_3$ | N | |
| 1.120 | CH$_3$ | Cl | H | OCH$_3$ | OCH$_3$ | N | |
| 1.121 | C$_2$H$_5$ | Cl | H | OCH$_3$ | OCH$_3$ | N | 202 (decomp.) |
| 1.122 | n-C$_3$H$_7$ | Cl | H | OCH$_3$ | OCH$_3$ | N | |
| 1.123 | i-C$_3$H$_7$ | Cl | H | OCH$_3$ | OCH$_3$ | N | 218–220 |
| 1.124 | n-C$_4$H$_9$ | Cl | H | OCH$_3$ | OCH$_3$ | N | |
| 1.125 | i-C$_4$H$_9$ | Cl | H | OCH$_3$ | OCH$_3$ | N | |
| 1.126 | sec.-C$_4$H$_9$ | Cl | H | OCH$_3$ | OCH$_3$ | N | |
| 1.127 | CH$_2$—CH=CH$_2$ | Cl | H | OCH$_3$ | OCH$_3$ | N | |
| 1.128 | CH$_2$—C≡CH | Cl | H | OCH$_3$ | OCH$_3$ | N | |
| 1.129 | CH$_2$—CH$_2$Cl | Cl | H | OCH$_3$ | OCH$_3$ | N | 194–196 |
| 1.130 | CH$_2$—CH$_2$—O—CH$_3$ | Cl | H | OCH$_3$ | OCH$_3$ | N | |
| 1.131 | CH$_2$—CH$_2$—O—CH$_3$ | F | H | OCH$_3$ | OCH$_3$ | N | 179–182 |
| 1.132 | CH$_2$—CH$_2$—O—CH$_2$—CH$_2$Cl | Cl | H | OCH$_3$ | OCH$_3$ | N | 198 (decomp.) |
| 1.133 | CH$_3$ | F | CH$_3$ | CH$_3$ | OCH$_3$ | N | |
| 1.134 | C$_2$H$_5$ | F | CH$_3$ | CH$_3$ | OCH$_3$ | N | |
| 1.135 | n-C$_3$H$_7$ | F | CH$_3$ | CH$_3$ | OCH$_3$ | N | |
| 1.136 | i-C$_3$H$_7$ | F | CH$_3$ | CH$_3$ | OCH$_3$ | N | |
| 1.137 | n-C$_4$H$_9$ | F | CH$_3$ | CH$_3$ | OCH$_3$ | N | |
| 1.138 | i-C$_4$H$_9$ | F | CH$_3$ | CH$_3$ | OCH$_3$ | N | |
| 1.139 | sec.-C$_4$H$_9$ | F | CH$_3$ | CH$_3$ | OCH$_3$ | N | |
| 1.140 | CH$_2$—CH=CH$_2$ | F | CH$_3$ | CH$_3$ | OCH$_3$ | N | |
| 1.141 | CH$_2$—C≡CH | F | CH$_3$ | CH$_3$ | OCH$_3$ | N | |
| 1.142 | CH$_2$—CH$_2$Cl | F | CH$_3$ | CH$_3$ | OCH$_3$ | N | |

TABLE 1-continued

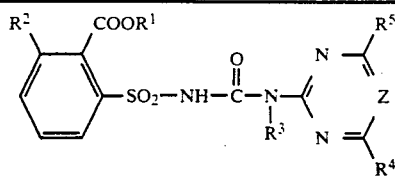

| Compound No. | R¹ | R² | R³ | R⁴ | R⁵ | Z | mp. [°C.] |
|---|---|---|---|---|---|---|---|
| 1.143 | CH₂—CH₂—O—CH₃ | F | CH₃ | CH₃ | OCH₃ | N | |
| 1.144 | CH₂—CH₂—O—CH₂—CH₂Cl | F | CH₃ | CH₃ | OCH₃ | N | |
| 1.145 | CH₃ | Br | H | CH₃ | OCH₃ | N | 202–205 |
| 1.146 | C₂H₅ | Br | H | CH₃ | OCH₃ | N | |
| 1.147 | n-C₃H₇ | Br | H | CH₃ | OCH₃ | N | |
| 1.148 | i-C₃H₇ | Br | H | CH₃ | OCH₃ | N | 197–199 |
| 1.149 | n-C₄H₉ | Br | H | CH₃ | OCH₃ | N | |
| 1.150 | i-C₄H₉ | Br | H | CH₃ | OCH₃ | N | |
| 1.151 | sec.-C₄H₉ | Br | H | CH₃ | OCH₃ | N | |
| 1.152 | CH₂—CH=CH₂ | Br | H | CH₃ | OCH₃ | N | |
| 1.153 | CH₂—C≡CH | Br | H | CH₃ | OCH₃ | N | |
| 1.154 | CH₂—CH₂Cl | Br | H | CH₃ | OCH₃ | N | |
| 1.155 | CH₂—CH₂—O—CH₃ | Br | H | CH₃ | OCH₃ | N | |
| 1.156 | CH₂—CH₂—O—CH₂—CH₂Cl | Br | H | CH₃ | OCH₃ | N | |
| 1.157 | CH₃ | Br | H | OCH₃ | OCH₃ | N | 216–218 |
| 1.158 | C₂H₅ | Br | H | OCH₃ | OCH₃ | N | |
| 1.159 | n-C₃H₇ | Br | H | OCH₃ | OCH₃ | N | |
| 1.160 | i-C₃H₇ | Br | H | OCH₃ | OCH₃ | N | 210 (decomp.) |
| 1.161 | n-C₄H₉ | Br | H | OCH₃ | OCH₃ | N | |
| 1.162 | i-C₄H₉ | Br | H | OCH₃ | OCH₃ | N | |
| 1.163 | sec.-C₄H₉ | Br | H | OCH₃ | OCH₃ | N | |
| 1.164 | CH₂—CH=CH₂ | Br | H | OCH₃ | OCH₃ | N | |
| 1.165 | CH₂—C≡CH | Br | H | OCH₃ | OCH₃ | N | |
| 1.166 | CH₂—CH₂Cl | Br | H | OCH₃ | OCH₃ | N | |
| 1.167 | CH₂—CH₂—O—CH₃ | Br | H | OCH₃ | OCH₃ | N | |
| 1.168 | CH₂—CH₂—O—CH₂—CH₂Cl | Br | H | OCH₃ | OCH₃ | N | |
| 1.169 | CH₃ | F | CH₃ | Cl | OCH₃ | N | |
| 1.170 | C₂H₅ | F | CH₃ | Cl | OCH₃ | N | |
| 1.171 | n-C₃H₇ | F | CH₃ | Cl | OCH₃ | N | |
| 1.172 | i-C₃H₇ | F | CH₃ | Cl | OCH₃ | N | |
| 1.173 | CH₃ | Br | H | Cl | OCH₃ | CH | 225–228 |
| 1.174 | C₂H₅ | Br | H | Cl | OCH₃ | CH | |
| 1.175 | n-C₃H₇ | Br | H | Cl | OCH₃ | CH | |
| 1.176 | CH₃ | F | CH₃ | Cl | OCH₃ | CH | 144–148 |

TABLE 2

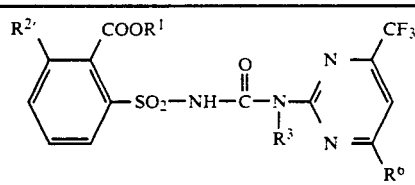

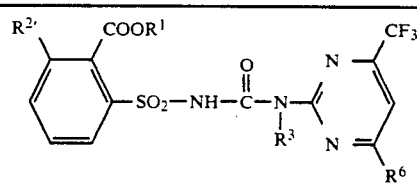

| Compound No. | R¹ | R²' | R³ | R⁶ | mp. [°C.] |
|---|---|---|---|---|---|
| 2.1 | CH₃ | H | H | H | 160–168 |
| 2.2 | CH₃ | H | H | Cl | 176–177 |
| 2.3 | C₂H₅ | H | H | Cl | |
| 2.4 | n-C₃H₇ | H | H | Cl | |
| 2.5 | n-C₄H₉ | H | H | Cl | |
| 2.6 | i-C₃H₇ | H | H | Cl | |
| 2.7 | sec-C₄H₉ | H | H | Cl | |
| 2.8 | CH₂CH=CH₂ | H | H | Cl | |
| 2.9 | CH₂C≡CH | H | H | Cl | |
| 2.10 | CH₂CH₂Cl | H | H | Cl | |
| 2.11 | CH₂CH₂OCH₃ | H | H | Cl | |
| 2.12 | CH₃ | H | H | OCH₃ | 150–151 |
| 2.13 | C₂H₅ | H | H | OCH₃ | 147–149 |
| 2.14 | n-C₃H₇ | H | H | OCH₃ | 200–202 |
| 2.15 | n-C₄H₉ | H | H | OCH₃ | |
| 2.16 | i-C₃H₇ | H | H | OCH₃ | |
| 2.17 | sec-C₄H₉ | H | H | OCH₃ | |
| 2.18 | CH₂CH=CH₂ | H | H | OCH₃ | |
| 2.19 | CH₂C≡CH | H | H | OCH₃ | |
| 2.20 | CH₂CH₂Cl | H | H | OCH₃ | |
| 2.21 | CH₂CH₂OCH₃ | H | H | OCH₃ | |
| 2.22 | CH₃ | H | H | OC₂H₅ | 150–152 |
| 2.23 | C₂H₅ | H | H | OC₂H₅ | 130–132 |
| 2.24 | n-C₃H₇ | H | H | OC₂H₅ | |
| 2.25 | n-C₄H₉ | H | H | OC₂H₅ | |
| 2.26 | i-C₃H₇ | H | H | OC₂H₅ | |
| 2.27 | sec-C₄H₉ | H | H | OC₂H₅ | |
| 2.28 | CH₂CH=CH₂ | H | H | OC₂H₅ | |
| 2.29 | CH₂C≡CH | H | H | OC₂H₅ | |
| 2.30 | CH₂CH₂Cl | H | H | OC₂H₅ | |
| 2.31 | CH₂CH₂OCH₃ | H | H | OC₂H₅ | |
| 2.32 | CH₃ | H | H | O-i-C₃H₇ | 170–173 |
| 2.33 | C₂H₅ | H | H | O-i-C₃H₇ | |
| 2.34 | n-C₃H₇ | H | H | O-i-C₃H₇ | |
| 2.35 | n-C₄H₉ | H | H | O-i-C₃H₇ | |
| 2.36 | i-C₃H₇ | H | H | O-i-C₃H₇ | |
| 2.37 | sec-C₄H₉ | H | H | O-i-C₃H₇ | |
| 2.38 | CH₂CH=CH₂ | H | H | O-i-C₃H₇ | |
| 2.39 | CH₂C≡CH | H | H | O-i-C₃H₇ | |
| 2.40 | CH₂CH₂Cl | H | H | O-i-C₃H₇ | |
| 2.41 | CH₂CH₂OCH₃ | H | H | O-i-C₃H₇ | |
| 2.42 | CH₃ | H | H | O-n-C₃H₇ | |

TABLE 2-continued

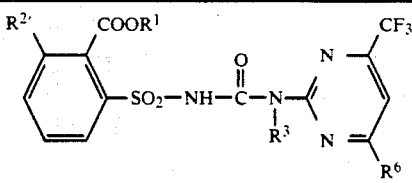

| Compound No. | R¹ | R²' | R³ | R⁶ | mp. [°C.] |
|---|---|---|---|---|---|
| 2.43 | $C_2H_5$ | H | H | $O\text{-}n\text{-}C_3H_7$ | |
| 2.44 | $n\text{-}C_3H_7$ | H | H | $O\text{-}n\text{-}C_3H_7$ | |
| 2.45 | $n\text{-}C_4H_9$ | H | H | $O\text{-}n\text{-}C_3H_7$ | |
| 2.46 | $i\text{-}C_3H_7$ | H | H | $O\text{-}n\text{-}C_3H_7$ | |
| 2.47 | $sec\text{-}C_4H_9$ | H | H | $O\text{-}n\text{-}C_3H_7$ | |
| 2.48 | $CH_2CH=CH_2$ | H | H | $O\text{-}n\text{-}C_3H_7$ | |
| 2.49 | $CH_2C\equiv CH$ | H | H | $O\text{-}n\text{-}C_3H_7$ | |
| 2.50 | $CH_2CH_2Cl$ | H | H | $O\text{-}n\text{-}C_3H_7$ | |
| 2.51 | $CH_2CH_2OCH_3$ | H | H | $O\text{-}n\text{-}C_3H_7$ | |
| 2.52 | $CH_3$ | H | H | $NHCH_3$ | 115–117 |
| 2.53 | $C_2H_5$ | H | H | $NHCH_3$ | |
| 2.54 | $n\text{-}C_3H_7$ | H | H | $NHCH_3$ | |
| 2.55 | $n\text{-}C_4H_9$ | H | H | $NHCH_3$ | |
| 2.56 | $i\text{-}C_3H_7$ | H | H | $NHCH_3$ | |
| 2.57 | $sec\text{-}C_4H_9$ | H | H | $NHCH_3$ | |
| 2.58 | $CH_2CH=CH_2$ | H | H | $NHCH_3$ | |
| 2.59 | $CH_2C\equiv CH$ | H | H | $NHCH_3$ | |
| 2.60 | $CH_2CH_2Cl$ | H | H | $NHCH_3$ | |
| 2.61 | $CH_2CH_2OCH_3$ | H | H | $NHCH_3$ | |
| 2.62 | $CH_3$ | H | H | $SCH_3$ | 155–157 |
| 2.63 | $C_2H_5$ | H | H | $SCH_3$ | 114–117 |
| 2.64 | $n\text{-}C_3H_7$ | H | H | $SCH_3$ | 146–148 |
| 2.65 | $n\text{-}C_4H_9$ | H | H | $SCH_3$ | |
| 2.66 | $i\text{-}C_3H_7$ | H | H | $SCH_3$ | |
| 2.67 | $sec\text{-}C_4H_9$ | H | H | $SCH_3$ | |
| 2.68 | $CH_2CH=CH_2$ | H | H | $SCH_3$ | |
| 2.69 | $CH_2C\equiv CH$ | H | H | $SCH_3$ | |
| 2.70 | $CH_2CH_2Cl$ | H | H | $SCH_3$ | |
| 2.71 | $CH_2CH_2OCH_3$ | H | H | $SCH_3$ | |
| 2.72 | $CH_3$ | H | H | $SC_2H_5$ | 71–73 |
| 2.73 | $C_2H_5$ | H | H | $SC_2H_5$ | |
| 2.74 | $n\text{-}C_3H_7$ | H | H | $SC_2H_5$ | |
| 2.75 | $n\text{-}C_4H_9$ | H | H | $SC_2H_5$ | |
| 2.76 | $i\text{-}C_3H_7$ | H | H | $SC_2H_5$ | |
| 2.77 | $sec\text{-}C_4H_9$ | H | H | $SC_2H_5$ | |
| 2.78 | $CH_2CH=CH_2$ | H | H | $SC_2H_5$ | |
| 2.79 | $CH_2C\equiv CH$ | H | H | $SC_2H_5$ | |
| 2.80 | $CH_2CH_2Cl$ | H | H | $SC_2H_5$ | |
| 2.81 | $CH_2CH_2OCH_3$ | H | H | $SC_2H_5$ | |
| 2.82 | $CH_3$ | H | H | $SC_3H_7$ | 188–189 |
| 2.83 | $n\text{-}C_3H_7$ | H | H | $SC_3H_7$ | 146–148 |
| 2.84 | $CH_3$ | H | $CH_3$ | Cl | |
| 2.85 | $C_2H_5$ | H | $CH_3$ | Cl | |
| 2.86 | $n\text{-}C_3H_7$ | H | $CH_3$ | Cl | |
| 2.87 | $n\text{-}C_4H_9$ | H | $CH_3$ | Cl | |
| 2.88 | $i\text{-}C_3H_7$ | H | $CH_3$ | Cl | |
| 2.89 | $sec\text{-}C_4H_9$ | H | $CH_3$ | Cl | |
| 2.90 | $CH_2CH=CH_2$ | H | $CH_3$ | Cl | |
| 2.91 | $CH_2C\equiv CH$ | H | $CH_3$ | Cl | |
| 2.92 | $CH_2CH_2Cl$ | H | $CH_3$ | Cl | |
| 2.93 | $CH_2CH_2OCH_3$ | H | $CH_3$ | Cl | |
| 2.94 | $CH_3$ | H | $CH_3$ | $OCH_3$ | 137–139 |
| 2.95 | $C_2H_5$ | H | $CH_3$ | $OCH_3$ | |
| 2.96 | $n\text{-}C_3H_7$ | H | $CH_3$ | $OCH_3$ | |
| 2.97 | $n\text{-}C_4H_9$ | H | $CH_3$ | $OCH_3$ | |
| 2.98 | $i\text{-}C_3H_7$ | H | $CH_3$ | $OCH_3$ | |
| 2.99 | $sec\text{-}C_4H_9$ | H | $CH_3$ | $OCH_3$ | |
| 2.100 | $CH_2CH=CH_2$ | H | $CH_3$ | $OCH_3$ | |
| 2.101 | $CH_2C\equiv CH$ | H | $CH_3$ | $OCH_3$ | |
| 2.102 | $CH_2CH_2Cl$ | H | $CH_3$ | $OCH_3$ | |
| 2.103 | $CH_2CH_2OCH_3$ | H | $CH_3$ | $OCH_3$ | |
| 2.104 | $CH_3$ | H | $CH_3$ | $NHCH_3$ | |
| 2.105 | $C_2H_5$ | H | $CH_3$ | $NHCH_3$ | |
| 2.106 | $n\text{-}C_3H_7$ | H | $CH_3$ | $NHCH_3$ | |
| 2.107 | $n\text{-}C_4H_9$ | H | $CH_3$ | $NHCH_3$ | |
| 2.108 | $i\text{-}C_3H_7$ | H | $CH_3$ | $NHCH_3$ | |
| 2.109 | $sec\text{-}C_4H_9$ | H | $CH_3$ | $NHCH_3$ | |
| 2.110 | $CH_2CH=CH_2$ | H | $CH_3$ | $NHCH_3$ | |
| 2.111 | $CH_2C\equiv CH$ | H | $CH_3$ | $NHCH_3$ | |
| 2.112 | $CH_2CH_2Cl$ | H | $CH_3$ | $NHCH_3$ | |
| 2.113 | $CH_2CH_2OCH_3$ | H | $CH_3$ | $NHCH_3$ | |
| 2.114 | $CH_3$ | Cl | H | Cl | |
| 2.115 | $C_2H_5$ | Cl | H | Cl | |
| 2.116 | $n\text{-}C_3H_7$ | Cl | H | Cl | |
| 2.117 | $n\text{-}C_4H_9$ | Cl | H | Cl | |
| 2.118 | $i\text{-}C_3H_7$ | Cl | H | Cl | |
| 2.119 | $sec\text{-}C_4H_9$ | Cl | H | Cl | |
| 2.120 | $CH_2CH=CH_2$ | Cl | H | Cl | |
| 2.121 | $CH_2C\equiv CH$ | Cl | H | Cl | |
| 2.122 | $CH_2CH_2Cl$ | Cl | H | Cl | |
| 2.123 | $CH_2CH_2OCH_3$ | Cl | H | Cl | |
| 2.124 | $CH_3$ | Cl | H | $OCH_3$ | 208–211 |
| 2.125 | $C_2H_5$ | Cl | H | $OCH_3$ | |
| 2.126 | $n\text{-}C_3H_7$ | Cl | H | $OCH_3$ | |
| 2.127 | $n\text{-}C_4H_9$ | Cl | H | $OCH_3$ | |
| 2.128 | $i\text{-}C_3H_7$ | Cl | H | $OCH_3$ | |
| 2.129 | $sec\text{-}C_4H_9$ | Cl | H | $OCH_3$ | |
| 2.130 | $CH_2CH=CH_2$ | Cl | H | $OCH_3$ | |
| 2.131 | $CH_2C\equiv CH$ | Cl | H | $OCH_3$ | |
| 2.132 | $CH_2CH_2Cl$ | Cl | H | $OCH_3$ | |
| 2.133 | $CH_2CH_2OCH_3$ | Cl | H | $OCH_3$ | |
| 2.134 | $CH_3$ | Cl | H | $SCH_3$ | 204–206 |
| 2.135 | $CH_3$ | Cl | $CH_3$ | Cl | |
| 2.136 | $C_2H_5$ | Cl | $CH_3$ | Cl | |
| 2.137 | $n\text{-}C_3H_7$ | Cl | $CH_3$ | Cl | |
| 2.138 | $n\text{-}C_4H_9$ | Cl | $CH_3$ | Cl | |
| 2.139 | $i\text{-}C_3H_7$ | Cl | $CH_3$ | Cl | |
| 2.140 | $sec\text{-}C_4H_9$ | Cl | $CH_3$ | Cl | |
| 2.141 | $CH_2CH=CH_2$ | Cl | $CH_3$ | Cl | |
| 2.142 | $CH_2C\equiv CH$ | Cl | $CH_3$ | Cl | |
| 2.143 | $CH_2CH_2Cl$ | Cl | $CH_3$ | Cl | |
| 2.144 | $CH_2CH_2OCH_3$ | Cl | $CH_3$ | Cl | |
| 2.145 | $CH_3$ | Cl | $CH_3$ | $OCH_3$ | |
| 2.146 | $C_2H_5$ | Cl | $CH_3$ | $OCH_3$ | |
| 2.147 | $n\text{-}C_3H_7$ | Cl | $CH_3$ | $OCH_3$ | |
| 2.148 | $n\text{-}C_4H_9$ | Cl | $CH_3$ | $OCH_3$ | |
| 2.149 | $i\text{-}C_3H_7$ | Cl | $CH_3$ | $OCH_3$ | |
| 2.150 | $sec\text{-}C_4H_9$ | Cl | $CH_3$ | $OCH_3$ | |
| 2.151 | $CH_2CH=CH_2$ | Cl | $CH_3$ | $OCH_3$ | |
| 2.152 | $CH_2C\equiv CH$ | Cl | $CH_3$ | $OCH_3$ | |
| 2.153 | $CH_2CH_2Cl$ | Cl | $CH_3$ | $OCH_3$ | |
| 2.154 | $CH_2CH_2OCH_3$ | Cl | $CH_3$ | $OCH_3$ | |
| 2.155 | $CH_3$ | F | H | Cl | 86–87 |
| 2.156 | $C_2H_5$ | F | H | Cl | |
| 2.157 | $n\text{-}C_3H_7$ | F | H | Cl | |
| 2.158 | $n\text{-}C_4H_9$ | F | H | Cl | |
| 2.159 | $i\text{-}C_3H_7$ | F | H | Cl | |
| 2.160 | $sec\text{-}C_4H_9$ | F | H | Cl | |
| 2.161 | $CH_2CH=CH_2$ | F | H | Cl | |
| 2.162 | $CH_2C\equiv CH$ | F | H | Cl | |
| 2.163 | $CH_2CH_2Cl$ | F | H | Cl | |
| 2.164 | $CH_2CH_2OCH_3$ | F | H | Cl | |
| 2.165 | $CH_3$ | F | H | $OCH_3$ | 179–182 |
| 2.166 | $C_2H_5$ | F | H | $OCH_3$ | |
| 2.167 | $n\text{-}C_3H_7$ | F | H | $OCH_3$ | |
| 2.168 | $n\text{-}C_4H_9$ | F | H | $OCH_3$ | |
| 2.169 | $i\text{-}C_3H_7$ | F | H | $OCH_3$ | |
| 2.170 | $sec\text{-}C_4H_9$ | F | H | $OCH_3$ | |
| 2.171 | $CH_2CH=CH_2$ | F | H | $OCH_3$ | |
| 2.172 | $CH_2C\equiv CH$ | F | H | $OCH_3$ | |
| 2.173 | $CH_2CH_2Cl$ | F | H | $OCH_3$ | |
| 2.174 | $CH_2CH_2OCH_3$ | F | H | $OCH_3$ | |
| 2.175 | $CH_3$ | F | H | $SCH_3$ | 181–187 |
| 2.176 | $CH_3$ | F | $CH_3$ | Cl | |
| 2.177 | $C_2H_5$ | F | $CH_3$ | Cl | |
| 2.178 | $n\text{-}C_3H_7$ | F | $CH_3$ | Cl | |
| 2.179 | $n\text{-}C_4H_9$ | F | $CH_3$ | Cl | |
| 2.180 | $i\text{-}C_3H_7$ | F | $CH_3$ | Cl | |
| 2.181 | $sec\text{-}C_4H_9$ | F | $CH_3$ | Cl | |
| 2.182 | $CH_2CH=CH_2$ | F | $CH_3$ | Cl | |

TABLE 2-continued

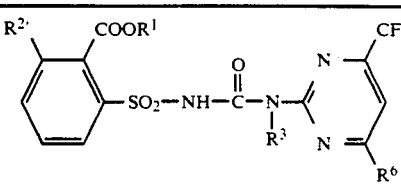

| Compound No. | $R^1$ | $R^{2'}$ | $R^3$ | $R^6$ | mp. [°C.] |
|---|---|---|---|---|---|
| 2.183 | $CH_2C\equiv CH$ | F | $CH_3$ | Cl | |
| 2.184 | $CH_2CH_2Cl$ | F | $CH_3$ | Cl | |
| 2.185 | $CH_2CH_2OCH_3$ | F | $CH_3$ | Cl | |
| 2.186 | $CH_3$ | F | $CH_3$ | $OCH_3$ | |
| 2.187 | $C_2H_5$ | F | $CH_3$ | $OCH_3$ | |
| 2.188 | $n-C_3H_7$ | F | $CH_3$ | $OCH_3$ | |
| 2.189 | $n-C_4H_9$ | F | $CH_3$ | $OCH_3$ | |
| 2.190 | $i-C_3H_7$ | F | $CH_3$ | $OCH_3$ | |
| 2.191 | $sec-C_4H_9$ | F | $CH_3$ | $OCH_3$ | |
| 2.192 | $CH_2CH=CH_2$ | F | $CH_3$ | $OCH_3$ | |
| 2.193 | $CH_2C\equiv CH$ | F | $CH_3$ | $OCH_3$ | |
| 2.194 | $CH_2CH_2Cl$ | F | $CH_3$ | $OCH_3$ | |
| 2.195 | $CH_2CH_2OCH_3$ | F | $CH_3$ | $OCH_3$ | |

TABLE 3

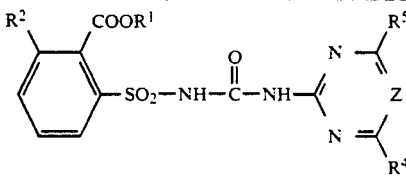

| $R^1$ | $R^2$ | $R^4$ | $R^5$ | Z |
|---|---|---|---|---|
| $CH_3$ | F | $OCH_3$ | Cl | CH |
| $C_2H_5$ | F | $OCH_3$ | Cl | CH |
| $n-C_3H_7$ | F | $OCH_3$ | Cl | CH |
| $CH_2CH_2-O-CH_3$ | F | $OCH_3$ | Cl | CH |
| $C_2H_5$ | Cl | $OCH_3$ | Cl | CH |
| $CH_3$ | Br | $OCH_3$ | Cl | CH |
| $CH_3$ | F | $OCH_3$ | $OCH_3$ | CH |
| $CH_2CH_2-O-CH_3$ | F | $OCH_3$ | $OCH_3$ | N |
| $CH_3$ | F | $CH_3$ | $OCH_3$ | CH |
| $CH_3$ | F | $CH_3$ | $OCH_3$ | N |
| $CH_3$ | F | $CH_3$ | $CH_3$ | CH |
| $CH_3$ | Cl | $CH_3$ | $CH_3$ | CH |

TABLE 3-continued

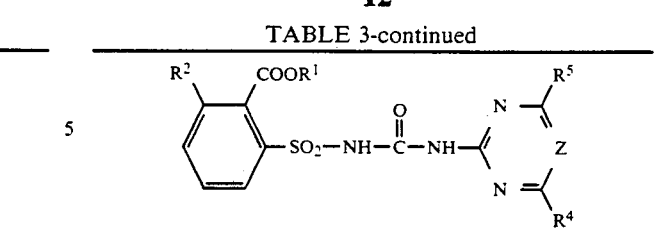

| $R^1$ | $R^2$ | $R^4$ | $R^5$ | Z |
|---|---|---|---|---|
| $C_2H_5$ | Cl | $CH_3$ | $CH_3$ | CH |
| $n-C_3H_7$ | Cl | $CH_3$ | $CH_3$ | CH |
| $i-C_3H_7$ | Cl | $CH_3$ | $CH_3$ | CH |
| $n-C_4H_9$ | Cl | $CH_3$ | $CH_3$ | CH |
| $i-C_4H_9$ | Cl | $CH_3$ | $CH_3$ | CH |
| $sec-C_4H_9$ | Cl | $CH_3$ | $CH_3$ | CH |
| $CH_2CH_2Cl$ | Cl | $CH_3$ | $CH_3$ | CH |
| $CH_2-CH=CH_2$ | Cl | $CH_3$ | $CH_3$ | CH |
| $CH_2-C\equiv CH$ | Cl | $CH_3$ | $CH_3$ | CH |

TABLE 4

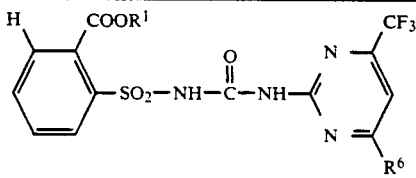

| $R^1$ | $R^6$ |
|---|---|
| $CH_3$ | Cl |
| $CH_3$ | $OCH_3$ |
| $C_2H_5$ | $OCH_3$ |
| $n-C_3H_7$ | $OCH_3$ |

Compounds Ia and Ib have acidic properties since the proton on the nitrogen atom present between the sulfonyl and the carbonyl group can readily be eliminated. With bases, the corresponding basic salts are therefore obtained. Examples of suitable bases are alkali metal or alkaline earth metal hydroxides, such as sodium hydroxide or potassium hydroxide, or alkali metal or alkaline earth metal alcoholates. Sodium methylate or potassium methylate is preferably used.

Suitable salts are listed in Table 5.

TABLE 5

Salts of the compounds Ia

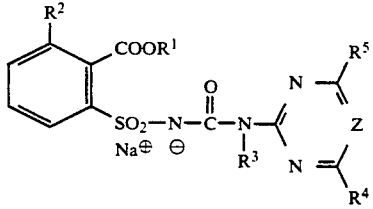

| Compound No. | $R^1$ | $R^2$ | $R^3$ | $R^4$ | $R^5$ | Z | mp. [°C.] |
|---|---|---|---|---|---|---|---|
| 3.1 | $CH_3$ | F | H | Cl | $OCH_3$ | CH | >300 |
| 3.2 | $C_2H_5$ | F | H | Cl | $OCH_3$ | CH | >300 |
| 3.3 | $n-C_3H_7$ | F | H | Cl | $OCH_3$ | CH | >300 |
| 3.4 | $i-C_3H_7$ | F | H | Cl | $OCH_3$ | CH | |
| 3.5 | $n-C_4H_9$ | F | H | Cl | $OCH_3$ | CH | |
| 3.6 | $i-C_4H_9$ | F | H | Cl | $OCH_3$ | CH | |
| 3.7 | $sec.-C_4H_9$ | F | H | Cl | $OCH_3$ | CH | |
| 3.8 | $CH_2-CH=CH_2$ | F | H | Cl | $OCH_3$ | CH | |
| 3.9 | $CH_2-CH_2Cl$ | F | H | Cl | $OCH_3$ | CH | |
| 3.10 | $CH_2-CH_2-O-CH_3$ | F | H | Cl | $OCH_3$ | CH | 167 (decomp.) |
| 3.11 | $CH_3$ | F | H | $CH_3$ | $OCH_3$ | CH | |
| 3.12 | $C_2H_5$ | F | H | $CH_3$ | $OCH_3$ | CH | >300 |

TABLE 5-continued
Salts of the compounds Ia

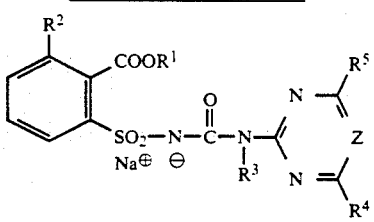

| Compound No. | R$^1$ | R$^2$ | R$^3$ | R$^4$ | R$^5$ | Z | mp. [°C.] |
|---|---|---|---|---|---|---|---|
| 3.13 | n-C$_3$H$_7$ | F | H | CH$_3$ | OCH$_3$ | CH | |
| 3.14 | CH$_3$ | Cl | H | OCH$_3$ | OCH$_3$ | CH | |
| 3.15 | C$_2$H$_5$ | Cl | H | OCH$_3$ | OCH$_3$ | CH | |
| 3.16 | n-C$_3$H$_7$ | Cl | H | OCH$_3$ | OCH$_3$ | CH | |
| 3.17 | i-C$_3$H$_7$ | Cl | H | OCH$_3$ | OCH$_3$ | N | 185 (decomp.) |
| 3.18 | CH$_2$—CH$_2$—O—CH$_3$ | Cl | H | OCH$_3$ | OCH$_3$ | CH | 154 |

Among the salts of the compounds Ia, the sodium salt of the following compound is particularly preferred.

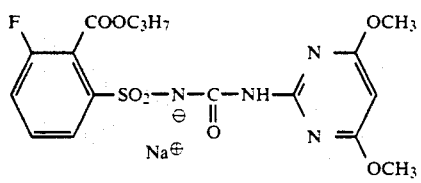

The phenylsulfonylureas Ia and Ib are disclosed in, for example, EP-A2 291 851 and EP-A 0 338 424 and can be prepared by the methods described there.

In principle, the phenylsulfonylureas Ia or Ib are obtainable a) by reacting an isocyanate of the formula IIIa

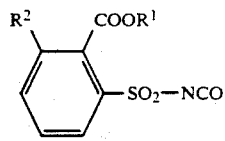

with an amine of the formula IVa

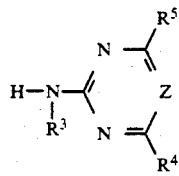

or by reacting an isocyanate of the formula IIIb

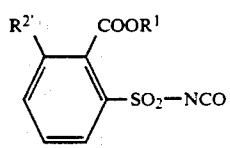

with an amine of the formula IVb

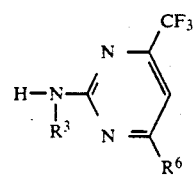

or b) by reacting a sulfonamide of the formula Va

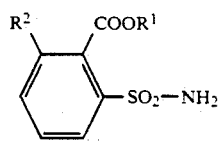

with a phenyl carbamate of the formula VIa

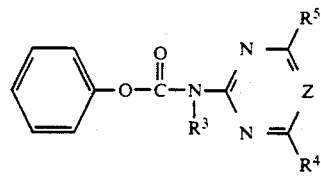

or by reacting a sulfonamide of the formula Vb

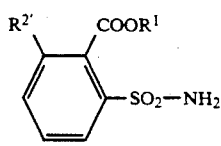

with a phenyl carbamate of the formula VIb

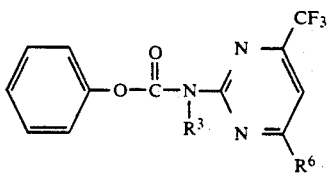

c) by reacting a phenyl carbamate of the formula VIIa

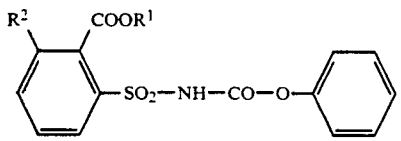

with an amine of the formula IVa or by reacting a phenyl carbamate of the formula VIIb

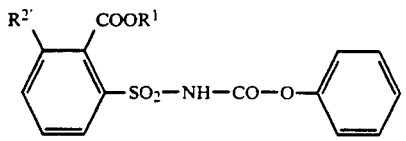

with an amine of the formula IVb.

The phenylsulfonylureas Ia and Ib are suitable as defoliants for cotton plants before harvesting of the bolls. They act at very low application rates and effectively prevent the growth of new shoots. In the case of the said ureas, defoliation of green leaves predominates over the desiccation effect, ie. defoliation with accompanying withering symptoms. This leads to higher fiber quality after the harvest.

The phenylsulfonylureas can be used, for example, in the form of directly sprayable solutions, powders, suspensions, including concentrated aqueous, oily or other suspensions or dispersions, emulsions, oil dispersions, pastes, dusts, broadcasting agents or granules, by spraying, atomizing, dusting, broadcasting or pouring. The application forms depend entirely on the intended uses; they should in any case ensure very fine distribution of the novel active ingredients.

Mineral oil fractions having a medium to high boiling point, such as kerosene or diesel oil, coal tar oils and oils of vegetable or animal origin, aliphatic, cyclic and aromatic hydrocarbons, eg. benzene, toluene, xylene, paraffin, tetrahydronaphthalene, alkylated naphthalenes or derivatives thereof, for example methanol, ethanol, propanol, butanol, chloroform, carbon tetrachloride, cyclohexanol, cyclohexanone, chlorobenzene or isophorone, or strongly polar solvents, such as dimethylformamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (spray powders, oil dispersions) by adding water. For the preparation of emulsions, pastes or oil dispersions, the substances as such, dissolved in an oil or solvent, can be homogenized in water by means of wetting agents, adhesives, dispersants or emulsifiers. However, concentrates which consist of active substance, wetting agents, adhesives, dispersants or emulsifiers and possibly solvents or oil and which are suitable for dilution with water can also be prepared.

Suitable surfactants are alkali metal, alkaline earth metal and ammonium salts of ligninsulfonic acid, naphthalenesulfonic acid, phenylsulfonic acid, alkylarylsulfonates, alkyl sulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, octadecanols, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powder, broadcasting, coated, impregnated and homogeneous granules can be prepared by binding the active ingredients to solid carriers. Solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, eg. ammonium sulfate, ammonium phosphate, ammonium nitrate, ureas and plant products, such as cereal meal, ground bark, woodmeal and nutshell meal, cellulose powder and other solid carriers.

The formulations contain from 0.1 to 95, preferably from 0.5 to 90, % by weight of active ingredient.

Examples of such formulations are:

I. A solution of 90 parts by weight of compound No. 1.13 and 10 parts by weight of N-methyl-α-pyrrolidone which is suitable for use in the form of very small drops;

II. A mixture of 20 parts by weight of compound No. 1.25, 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid, 5 parts by weight of the adduct and 40 moles of ethylene oxide with 1 mole of castor oil; a dispersion is obtained by finely distributing the solution in water;

III. An aqueous dispersion of 20 parts by weight of compound No. 1.36, 40 parts by weight of cyclohexanone, 30 parts by weight of isobutanol and 20 parts by weight of the adduct of 40 moles of ethylene oxide with 1 mole of castor oil;

IV. An aqueous dispersion of 20 parts by weight of compound No. 1.60, 25 parts by weight of cyclohexanol, 65 parts by weight of a mineral oil fraction boiling within the range from 210° to 280° C. and 10 part by weight of the adduct of 40 moles of ethylene oxide with 1 mole of castor oil;

V. A mixture milled in a hammer mill and consisting of 80 parts by weight of compound No. 1.73, 3 parts by weight of the sodium salt of diisobutylnaphthalene-α-sulfonic acid, 10 parts by weight of the sodium salt of a ligninsulfonic acid from a sulfite waste liquor and 7 parts by weight of silica gel powder; a spray liquor is obtained by finely distributing the mixture in water;

VI. A thorough mixture of 3 parts by weight of compound No. 1.84 and 97 parts by weight of finely divided kaolin; this dust contains 3% by weight of active ingredient;

VII. A thorough mixture of 30 parts by weight of compound No. 2.12, 92 parts by weight of silica gel powder and 8 parts by weight of liquid paraffin, which has been sprayed onto the surface of this silica gel; this formulation gives the active ingredient good adhesive power;

VIII. A stable aqueous dispersion of 40 parts by weight of compound No. 2.62, 10 parts by weight of the sodium salt of a phenolsulfonic acid/urea/formaldehyde condensate, 2 parts by weight of silica gel and 48 parts by weight of water, which dispersion can be further diluted;

IX. A mixture milled in a hammer mill and consisting of 10 parts by weight of compound No. 3.17, 4 parts by weight of the sodium salt of diisobutylnaphthalene-α-sulfonic acid, 20 parts by weight of the sodium salt of a ligninsulfonic acid from a sulfite waste liquor, 38 parts by weight of silica gel and 38 parts by weight of kaolin. A spray liquor which contains 0.1% by weight of the active ingredient is obtained by finely distributing the mixture in 10,000 parts by weight of water.

The action and the rate of action can be promoted, for example, by additives which increase the effect, such as organic solvents, wetting agents and oils. This permits a reduction in the application rate of the actual active ingredient.

The agents are fed to the plants mainly by spraying the foliage. Application may be effected, for example, using water as the carrier, by conventional spraying methods with about 100–1,000 l/ha of spray liquor. The agents can be used by the low volume and ultralow volume methods as well as being applied in the form of microgranules.

The novel agents can be used in application rates of from 0.1 to 3,000, preferably from 0.5 to 1,000, in particular from 1 to 500, g/ha.

The agents can be used either alone or as a mixture with other agents or with other active ingredients. If necessary, other defoliants, desiccants, crop section agents or pesticides may be added, depending on the intended use.

We have also found that mixtures of the novel agents, for example with the active ingredients (A)-(C) stated below, lead to even better control of the undesirable resprouting of plants after desiccation or defoliation in cotton. The successful defoliation is retained or even enhanced:

(A) Herbicidal active ingredients a. Chloroacetanilides, such as 2-chloro-N-(2,6-dimethylphenyl)-N-(1H-pyrazol-1-ylmethyl)-acetamide (common name: metazochlor), described in DE-A 26 48 008, b. Substituted quinoline-8-carboxylic acids, such as 3,7-dichloroquinoline-8-carboxylic acid, described in EP-A-104 389, and 3-methyl-7-chloroquinoline-8-carboxylic acid, described in EP-A-60 429, c. Cyclohexenone derivatives, such as 2-[(1-ethoximino)-butyl]-5-[2-(ethylthio)-propyl]-3-hydroxy-2-cyclohexen-1-one (common name: sethoxydim), described in DE-A 28 22 304, and 2-[1-(ethoximino)-butyl]-3-hydroxy-5-(2H-tetrahydrothiopyran-3-yl)-2-cyclohexen-1-one (common name: cycloxydim), described in DE-A 31 21 355, d. Phenoxyalkanecarboxylic acids, such as (4-chloro-2-methylphenoxy)-acetic acid, e. 3-Isopropyl-1H-2,1,3-benzothiadiazin-4(3H)-one 2,2-dioxide, described in DE-A 15 42 836, f. Dinitroanilines, such as N-(1-ethylpropyl)-3,4-dimethyl-2,6-dinitroaniline, described in DE-A 22 41 408, g. Imidazolinones, eg. 2-[4,5-dihydro-4-methyl-4-(1-methylethyl)-5-oxo-1H-imidazol-2-yl]-3-quinolinecarboxylic acid, h. 3,4,5,6-Tetrahydrophthalimides, such as N-[5-(ethyl α-chloroacrylate)-4-chlorophenyl]-3,4,5,6-tetrahydrophthalimide, described in EP-A 0 240 659, and i. Diphenyl ethers, such as the sodium salt of 5-[2-chloro-4-(trifluoromethyl)-phenoxy]-2-nitrobenzoate, described in DE-A 23 11 638.

Preferred components of the mixture are:
2-methyl-6-ethylethoxymethyl-2-chloroacetanilide
2-methyl-6-ethyl-N-(methoxy-1-methylethyl)-2-chloroacetanilide
2,6-dimethyl-N-(1H-pyrazol-1-ylmethyl)-2-chloroacetanilide
2,6-diethyl-N-(methoxymethyl)-2-chloroacetanilide
3-methyl-7-chloroquinoline-8-carboxylic acid (salts, esters)
3,7-dichloroquinoline-8-carboxylic acid (salts, esters)
2-[(1-ethoximino)-butyl]-5-[2-(ethylthio)-propyl]-3-hydroxy-2-cyclohexan-1-one (salts)
2-[(1-trans-chloroallyloximino)-butyl]-5-[2-(ethylthio)-propyl]-3-hydroxy-2-cyclohexan-1-one (salts)
2-[(1-trans-chloroallyloximino)-propyl]-5-[2-(ethylthio)propyl]-3-hydroxy-2-cyclohexan-1-one (salts)
2-[(1-ethoximino)-butyl]-5-[2H-tetrahydrothiopyran-3-yl)3-hydroxy-2-cyclohexan-1-one (salts)
2-[(1-ethoximino)-propyl]-5-(2,4,6-trimethylphenyl)-3-hydroxy-2-cyclohexan-1-one (salts)
2-methyl-4-chlorophenoxyacetic acid (salts, esters, amides)
2-[2-methyl-4-chlorophenoxy]-propionic acid (salts, esters, amides)
4-[2-methyl-4-chlorophenoxy]-butyric acid (salts, esters, amides)
4-[2,4-dichlorophenoxy]-butyric acid (salts, esters, amides)
2-[2,4-dichlorophenoxy]-propionic acid (salts, esters, amides)
2,4-dichlorophenoxyacetic acid (salts, esters, amides)
3,5,6-trichloropyrid-2-yloxyacetic acid (salts, esters, amides)
3-(1-methylethyl)-1H-2,1,3-benzothiadiazin-4(3H)-one 2,2-dioxide (salts)
3-(1-methylethyl)-1-cyano-2,1,3-benzothiadiazin-4(3H)-one 2,2-dioxide (salts)
N-(1-ethylpropyl)-3,4-dimethyl-2,6-dinitroaniline
2-[4,5-dihydro-4-methyl-4-(1-methylethyl)-5-oxo-1H-imidazol-2-yl]-3-quinolinecarboxylic acid
N-[5-(ethyl α-chloroacrylate)-4-chlorophenyl]-3,4,5,6-tetrahydrophthalimide
5-[2-chloro-4-(trifluoromethyl)-phenoxy]-2-nitrobenzoic acid (salts)
ethoxycarbonyl methyl 5-[2-chloro-4-(trifluoromethyl)-phenoxy]-2-nitrobenzoate
5-[2-chloro-4-(trifluoromethyl)-phenoxy]-2-nitrobenzoic acid methylsulfonylamide (B) Defoliants and desiccants These are generally known, for example from Cathey, G. W. (1986), Physiology of defoliation in cotton production, in Cotton Physiology (J. R. Mauney, J. McD. Stewart, eds.) The Cotton Foundation Reference Book Series No. 1, Chapter 14, 143–153, and from Morgan, P. W. (1985), Chemical manipulation of abscission and desiccation, in Agricultural Chemicals of the Future (J. L. Hilton, ed.) BARC Symposium 8, 61–74, Rowman & Allanheld, Ottawa.

a. Urea derivatives, such as N-phenyl-N'-1,2,3-thiadiazol-5-ylurea, disclosed in DE-A 25 06 690 and 26 19 861, N-phenyl-N,-1,3,4-thiadiazol-2-ylurea, described in DE-A 36 12 830, or N-phenyl-N'-2-chloro-pyrid-3-ylurea, described in DE-A 28 43 722,
b. (2-Chloroethyl)-phosphonic acid,
c. S,S,S-Tributyl phosphorotrithioate and S,S,S-tributyl phosphorotrithioite,
d. 2,3-Dihydro-5,6-dimethyl-1,4-dithiine-1,1,4,4-tetraoxide,
e. Salts of N-(phosphonomethyl)-glycine, such as the isopropylammonium salt,
f. Magnesium chlorate and sodium chlorate,
g. 1,2-Dihydropyridazine-3,6-dione,
h. 7-Oxabicyclo[2.2.1]heptane-2,3-dicarboxylic acid (common name: endothall),
i. 6,7-Dihydrodipyridol (1,2-α:2',1'-c)pyridilium ion as the dibromide monohydrate salt (common name: diquat) and 1,1,-dimethyl-4,4'-bipyridinium ion as the dichloride or dimethylsulfate salt (common name: paraquat)

Preferred components of the mixture are:
N-phenyl-N'-1,2,3-thiadiazol-5-ylurea
N-phenyl-N'-1,3,4-thiadiazol-2-ylurea
N-phenyl-N'-2-chloropyrid-3-ylurea
N-(3,4-dichlorophenyl)-N',N'-dimethylurea
2-chloroethylphosphonic acid
S,S,S-tributyl phosphorotrithioate, S,S,S-tributyl phosphorotrithioite,
2,3-dihydro-5,6-dimethyl-1,4-dithiine 1,1,4,4-tetraoxide
N-(phosphonomethyl)-glycine (salts)
1,2-dihydropyridazine-3,6-dione perchlorates
7-oxabicyclo[2.2.1]heptane-2,3-dicarboxylic acid (salts, esters, amides)
1,1-ethylene-2,2-bipyridilium dibromide (C) Growth retardants a. Quaternary ammonium salts from the group consisting
of the N,N-dimethylazacycloheptanium salts, N,N-dimethylpiperidinium salts, N,N-dimethylhexahydropyridazinium salts, N,N-dimethyltetrahydropyridazinium salts, N-methylpyridinium salts, N,N-dimethylpyrrolidinium salts and N,N,N-trimethyl-N-2-chloroethylammonium salts, in particular N-2-chloroethyl-N-trimethylammonium chloride (common name: chlormequat chloride) and N,N-dimethylpiperidinium chloride (common name: mepiquat chloride),
b. Pyrimidine compounds, as disclosed in U.S. Pat. No. 3,818,009 and in Journal of Plant Growth Regulation 7:27, 1988 (for example those with the common name ancymidol or flurprimidol),
c. Pyridine compounds which are disclosed in DE-A 30 15 025,
d. Norbornadiazetines, as described in DE-A 26 15 878 and 27 42 034,
e. Triazole compounds having a growth-regulating action, as described in European Application P 88 104 320.2, in British Crop Protection, Conference—Weeds 1982, Vol. 1, BCPC Publications, Croydon, 1982, page 3, in Plant Cell Physiol. 25, 611, in Pestic. Sci. 19, 153, in J. Agron. Crop Sci. 158, 324 or in J. Plant Growth Regul. 4, 181, eg. 1-phenoxy-3-(1H-1,2,4-triazol-1-yl)-4-hydroxy-5,5-dimethylhexane,
f. 2-Acyl-3-hydroxycyclohex-2-en-1-ones as described in EP-A 126 713 or 123 001,
g. 1-(4-Chlorophenoxy)-3,3-dimethyl-1-(1,2,4-triazol-1-yl)-butan-2-one (common name: triadimefon), N-[2,4-dimethyl-5-(trifluoromethylsulfonylamino)]-phenylacetamide (common name: mefluidide), 2-Chloro-2',6'-diethyl-N-(methoxymethyl)-acetanilide (common name: alachlor). S-Ethyl dipropylthiocarbamate (common name: EPTC), Succinic 2,2-dimethylhydrazide (common name: daminozid).

Preferred components of the mixture are:
N,N,N-Trimethyl-N-2-chloroethylammonium salts
N,N-Dimethylpiperidinium salts
N-Methylpyridinium salts
α-Cyclopropyl-α-(4-methoxyphenyl)-5-pyrimidinemethanol
α-Cyclopropyl-α-(4-trifluoromethoxyphenyl)-5-pyrimidinemethanol
5-(4-chlorophenyl)-3,4,5,9,10-pentaazatetracyclo[5.4.1.0$^{2,6}$.0$^{8,11}$]dodeca-3,9-diones    all-cis-8-(4-chlorophenyl)-3,4,8-triazatetracyclo[4.3.1.0$^{2,5}$.0$^{7,9}$]-dec-3-one
Succinic mono-N,N-dimethylhydrazide
Ethyl N,N-dipropylthiocarbamate
N-2,4-Dimethyl-5-(trifluoromethyl)-sulfonylaminophenylacetamide
1-(4-chlorophenoxy)-3,3-dimethyl-1-(1,2,4-triazol-1-yl)-2-butanone
2-propylcarbonyl-5-ethoxycarbonyl-3-hydroxy-2-cyclohexen-1-one
1-(1,2,4-triazol-1-yl)-1-methoxy-2-(2,4-dichlorophenyl)-propan-2-ol
2,2-dimethyl-4-(1,2,4-triazol-1-yl)-6-phenoxyhexan-3-ol
2,2-dimethyl-4-(1,2,4-triazol-1-yl)-5-(4-chlorophenyl)-pentan-3-ol
2,2-dimethyl-4-(1,2,4-triazol-1-yl)-5-(4-chlorophenyl)-pent-4-en-1-ol
2,2-dimethyl-4-(1,2,4-triazol-1-yl)-5-cyclohexylpent-4-en-3-ol
1-(5-methyl 1,3-dioxan-5-yl)-4-(1,2,4-triazol-1-yl)-4-(4-trifluoromethylphenyl)-propen-2-ol Particularly advantageous mixtures of the compounds Ia or Ib are obtained with substituted N-phenyl-3,4,5,6-tetrahydrophthalimides of the formula II

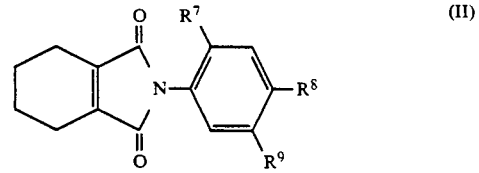
(II)

where
$R^7$ is hydrogen, fluorine or chlorine,
$R^8$ is chlorine and
$R^9$ is a) a radical

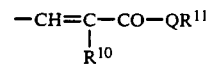

where
Q is oxygen or sulfur,
$R^{10}$ is hydrogen, chlorine, bromine, cyano or $C_1$–$C_6$-alkyl and
$R^{11}$ is hydrogen, $C_1$–$C_8$-alkyl, $C_1$–$C_8$-alkenyl, $C_3$- or $C_4$-alkynyl, $C_1$–$C_8$-alkoxyalkyl, $C_1$–$C_8$-alkylthioalkyl, phenyl-$C_1$–$C_8$-alkyl or $C_3$–$C_6$-cycloalkyl, or
b) a radical

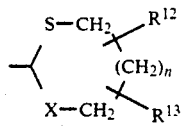

where
X is oxygen or sulfur,
n is 0 or 1,
$R^{12}$ is hydrogen or $C_1$-$C_4$-alkyl which may be substituted by hydroxyl, halogen, cyano, mercapto, $C_1$-$C_4$-alkoxy, $C_1$-$C_4$-alkylthio, $C_1$-$C_4$-alkylcarbonyloxy or $C_1$-$C_4$-alkoxycarbonyl-$C_1$-$C_4$-alkylthio, and
$R^{13}$ is hydrogen or $C_1$-$C_3$-alkyl, or c) a radical $OR^{14}$, where
$R^{14}$ is $C_1$-$C_4$-alkyl, $C_3$- or $C_4$-alkenyl, $C_3$- or $C_4$-alkynyl, $C_1$-$C_4$-alkylcarbonyl, $C_1$-$C_4$-alkoxycarbonyl-$C_1$-$C_4$-alkyl, tetrahydrofurfuryl, dihydropyranylmethyl, dihydrothiopyranylmethyl, tetrahydropyranylmethyl or tetrahydrothiopyranylmethyl.

The preparation of N-substituted tetrahydrophthalimides II is described in detail in German Patent Application DE-A . . . (Application No. P 39 05 916.2). They are obtainable from 3,4,5,6-tetrahydrophthalic anhydride and correspondingly substituted aniline derivatives, which can be obtained by reducing the corresponding nitro compounds. As a rule, the reaction is carried out in an inert solvent at from 20° to 200° C., preferably from 40° to 150° C. Examples of suitable solvents are lower alkanecarboxylic acids, such as glacial acetic acid or propionic acid, or aprotic solvents, such as toluene or xylene, in the presence of acidic catalysts, for example aromatic sulfonic acids. The preparation of the compounds II and IIa can be carried out similarly to the methods described in EP-A 240 659, 300 387, 300 398, 236 916, 313 963, 319 791 and 320 677 or DE-A-31 09 035 and 35 33 440 or GB-A 2 071 100.

The phenylsulfonylureas Ia or Ib and the tetrahydrophthalimides II can be used in weight ratios of from 100:1 to 1:100, but mixtures in a ratio of from 50:1 to 1:50 are preferably used.

USE EXAMPLES

The following were used as comparative agents

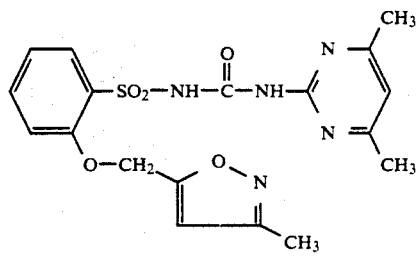

disclosed in DE-A 34 13 565 and
the synergistic agent

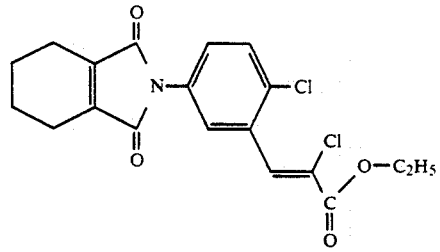

The comparative agents A, B and C were used in the form of their ready-formulated commercial products. Comparative agent E was formulated similarly to Formulation Example III (page 23) and comparative agent D and the phenylsulfonylureas Ia or Ib were formulated similarly to Formulation Example IX (page 24).

The amount of water in the formulations converts to 1,000 l/ha.

The test plants used were young 6-leaved cotton plants (without dicotyledons) of the variety Stoneville 825, which were grown under greenhouse conditions (relative humidity from 50 to 70%).

USE EXAMPLE 1

The leaves of the cotton plants were treated to runoff with aqueous formulations of the stated active ingredients (with the addition of 0.15% by weight, based on the spray liquor, of the fatty alcohol alkoxylate Plurafac LF 700). After 10 days, the number of dropped leaves and the degree of defoliation in % were determined. In the case of the untreated control plants, no leaf fall occurred. Resprouting of the plants was determined (day/night temperature 25°/18° C.).

| Agent, containing active ingredient No. | Converted application rate [kg/ha] | Defoliation [%] | Resprouting* |
|---|---|---|---|
| 1.13 | 0.016 | 80 | + |
| 1.25 | 0.016 | 69 | +++ |
| 1.36 | 0.016 | 50 | ++ |
| 1.60 | 0.016 | 86 | + |
| 1.84 | 0.016 | 73 | + |
| 1.108 | 0.016 | 68 | + |
| 2.12 | 0.016 | 95 | 0 |
| 2.62 | 0.016 | 61 | +++ |
| Comparative agent B | 0.500 | 46 | ++++ |

*Rating: ++++ pronounced, + slight resprouting; 0 no resprouting

The results of Use Example 1 show that, even at a low application rate, the novel agents lead to defoliation of the plants and efficiently suppress resprouting. They are clearly superior to the comparative agent.

USE EXAMPLE 2

Leaves of the cotton plants were treated to run-off with aqueous formulations of the stated active ingredients (with the addition of 0.15% by weight, based on the spray liquor, of the fatty alcohol alkoxylate Plurafac LF 700). After 9 days, the number of dropped leaves and the degree of defoliation were determined. In the case of the untreated control plants, no leaf fall occurred (day/night temperature 25°/18° C.).

| Agent. containing active ingredient No. | Converted application rate [kg/ha] | Defoliation [%] |
| --- | --- | --- |
| 1.36 | 0.031 | 74 |
| 1.48 | 0.031 | 61 |
| 1.72 | 0.031 | 65 |
| 1.73 | 0.031 | 80 |
| 1.74 | 0.031 | 35 |
| 1.4 | 0.031 | 31 |
| 3.17 | 0.031 | 60 |
| Comparative agent A | 0.062 | 16 |
| Comparative agent B | 0.031 | 4 |
| Comparative agent C | 0.031 | 27 |
| Comparative agent D | 0.031 | 0 |

The results of Use Example 2 show that the novel agents have a clearly superior action as defoliants compared with the active ingredients A, B and C and in particular the closely related compound D.

USE EXAMPLE 3

Leaves of the cotton plants were treated to run-off with aqueous formulations of the stated active ingredients (with the addition of 0.15% by weight, based on the spray liquor, of the fatty alcohol alkoxylate Plurafac LF 700). After 13 days, the number of dropped leaves and the degree of defoliation were determined. In the case of the untreated control plants, no leaf fall occurred. Resprouting of the plants was determined after 21 days (day/night temperature 26°/18° C.).

| Agent. containing active ingredient No. | Converted application rate [kg/ha] | Defoliation [%] | Resprouting* |
| --- | --- | --- | --- |
| 1.36 | 0.031 | 94 | +++ |
| 1.36 + E | 0.031 + 0.125 | 90 | ++ |
| E | 0.125 | 77 | ++++ |

*Rating: ++++ pronounced. + slight resprouting; 0 no resprouting

The results of Use Example 3 show that N-[5-(ethyl α-chloroacrylate)-4-chlorophenyl]-3,4,5,6-tetrahydrophthalimide E enhances the action of compound No. 1.36 against resprouting of the plants.

We claim:

1. A method for defoliating cotton plants, wherein an amount, having a defoliant effect, of a phenylsulfonylurea of the formula Ia or Ib

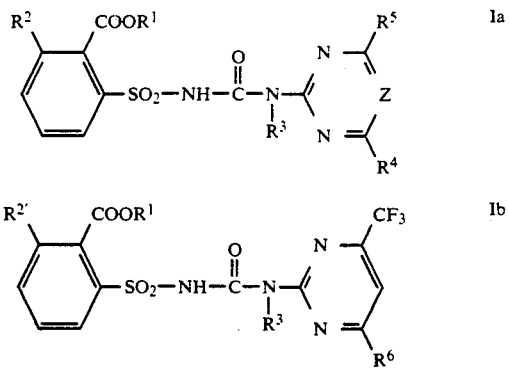

where $R^1$ is $C_1$-$C_4$-alkyl or $C_3$-$C_5$-alkoxyalkyl, and these radicals may each carry up to 3 halogen atoms, or $C_3$- or $C_4$-alkenyl or $C_3$- or $C_4$-alkynyl, $R^2$ is fluorine, chlorine or bromine, $R^{2'}$ is hydrogen, fluorine, chlorine or bromine, $R^3$ is hydrogen, methyl or ethyl, $R^4$ is halogen, methyl or methoxy, $R^5$ is methyl or methoxy, $R^6$ is halogen, $C_1$- or $C_2$-alkyl, $C_1$- or $C_2$-alkoxy, $C_1$- or $C_2$-alkylthio or $C_1$- or $C_2$-alkylamino and Z is CH or N, or an alkali metal or alkaline earth metal salt of a compound Ia or Ib is allowed to act on cotton plants.

2. A method for defoliating cotton plants, wherein an amount, having a defoliant effect, of a phenylsulfonylurea Ia as defined in claim 1, where $R^1$ is methyl, ethyl, n-propyl, isopropyl or 2-methoxyethyl, $R^2$ is fluorine, chlorine or bromine, $R^3$ is hydrogen or methyl, $R^4$ is chlorine, methyl or methoxy, $R^5$ is methyl or methoxy and Z is CH, is allowed to act on cotton plants.

3. A method for defoliating cotton, wherein an amount, having a defoliant effect, of a phenylsulfonylurea Ia as defined in claim 1, where $R^1$ is methyl, $R^2$ is fluorine, $R^3$ is hydrogen, $R^4$ and $R^5$ are each methyl or methoxy and Z is nitrogen, is allowed to act on cotton plants.

4. A method for defoliating cotton, wherein an amount, having a defoliant effect, of the sodium salt of a phenylsulfonylurea Ia as defined in claim 1, where $R^1$ is isopropyl, $R^2$ is fluorine, $R^3$ is hydrogen, $R^4$ and $R^5$ are each methoxy and Z is nitrogen, is allowed to act on cotton plants.

5. A method for defoliating cotton, wherein an amount, having a defoliant effect, of a phenylsulfonylurea Ib as defined in claim 1, where $R^1$ is methyl, ethyl or n-propyl, $R^{2'}$ and $R^3$ are each hydrogen and $R^6$ is chlorine, methoxy or methylthio, is allowed to act on cotton plants.

* * * * *

UNITED STATES PATENT AND TRADEMARK OFFICE
CERTIFICATE OF CORRECTION

PATENT NO. : 5,171,352

DATED : December 15, 1992

INVENTOR(S) : GROSSMANN et al.

It is certified that error appears in the above-identified patent and that said Letters Patent is hereby corrected as shown below:

On title page, Item [73] ASSIGNEE: BASF Aktiengesellschaft, Ludwigshafen, Fed. Rep. of Germany On title page, Item [56] Attorney, Agent, or Firm - Keil & Weinkauf Signed and Sealed this Nineteenth Day of October, 1993

Attest:

BRUCE LEHMAN

Attesting Officer

Commissioner of Patents and Trademarks